(12) United States Patent
Jung et al.

(10) Patent No.: US 11,214,928 B2
(45) Date of Patent: *Jan. 4, 2022

(54) METHOD OF MARKING CELLULOSIC PRODUCTS

(71) Applicant: Applied DNA Sciences, Inc., Stony Brook, NY (US)

(72) Inventors: Lawrence Jung, Dix Hills, NY (US); Michael E. Hogan, Stony Brook, NY (US); Ming Hwa Benjamin Liang, East Setauket, NY (US)

(73) Assignee: Applied DNA Sciences, Inc., Stony Brook, NY (US)

( * ) Notice: Subject to any disclaimer, the term of this patent is extended or adjusted under 35 U.S.C. 154(b) by 29 days.

This patent is subject to a terminal disclaimer.

(21) Appl. No.: 16/716,952

(22) Filed: Dec. 17, 2019

(65) Prior Publication Data

US 2020/0199820 A1 Jun. 25, 2020

Related U.S. Application Data

(63) Continuation of application No. 15/466,016, filed on Mar. 22, 2017, now Pat. No. 10,519,605.

(60) Provisional application No. 62/320,946, filed on Apr. 11, 2016.

(51) Int. Cl.
| | | |
|---|---|---|
| *D21H 21/44* | (2006.01) | |
| *C12Q 1/68* | (2018.01) | |
| *D01F 2/08* | (2006.01) | |
| *D21H 13/08* | (2006.01) | |
| *C08L 1/02* | (2006.01) | |
| *D01F 1/10* | (2006.01) | |
| *C12Q 1/6876* | (2018.01) | |
| *D01F 1/06* | (2006.01) | |
| *D01F 2/00* | (2006.01) | |
| *C08B 9/00* | (2006.01) | |

(52) U.S. Cl.
CPC ............... *D21H 21/44* (2013.01); *C08B 9/00* (2013.01); *C08L 1/02* (2013.01); *C12Q 1/68* (2013.01); *C12Q 1/6876* (2013.01); *D01F 1/06* (2013.01); *D01F 1/10* (2013.01); *D01F 2/00* (2013.01); *D01F 2/08* (2013.01); *D21H 13/08* (2013.01)

(58) Field of Classification Search
None
See application file for complete search history.

(56) References Cited

U.S. PATENT DOCUMENTS

2015/0018538 A1* 1/2015 Berrada ............... C12Q 1/6816
536/23.1

* cited by examiner

*Primary Examiner* — Samuel C Woolwine
(74) *Attorney, Agent, or Firm* — Lowndes, Drosdick, Doster & Reed.P.A; Jon M. Gibbs; Clay D. Shorrock

(57) ABSTRACT

Methods for marking cellulosic products, including cellulosic fibers such as lyocell and cellulosic films, including methods for marking such products with a detectable nucleic acid marker to identify and validate the origin or authenticity of the products or items manufactured using such products. Detectably-marked cellulosic products marked with nucleic acid markers for authentication, validation and tracking are also provided.

19 Claims, 3 Drawing Sheets

METHOD OF MARKING CELLULOSIC PRODUCTS

CROSS-REFERENCE TO RELATED APPLICATION

This application is a continuation of U.S. patent application Ser. No. 15/466,016, filed on Mar. 22, 2017, which claims the benefit of U.S. Provisional Patent Application Ser. No. 62/320,946 filed Apr. 11, 2016, the contents of which applications are herein incorporated by reference in their entirety.

TECHNICAL FIELD

The invention pertains to a method for marking cellulosic products, including cellulosic fibers and cellulosic films, and more particularly to a method for marking such products with a nucleic acid marker to identify and validate the origin or authenticity of the products or items manufactured using such products.

BACKGROUND OF THE INVENTION

Manufacturers have an interest in protecting the integrity and purity of their products that are fabricated from quality components and may be subject to mixing or dilution with less expensive, lower quality materials. Such adulteration and even outright counterfeit substitution of process feedstocks and production materials, received from suppliers to be processed by the manufacturers, often escapes detection until after the products are manufactured.

Counterfeiting and blending of high-end products in particular, with cheaper material, has become a major liability problem for many companies. The International Chamber of Commerce (ICC) reported that in 2008, counterfeited goods resulted in a loss of $650 billion in revenues and 2.5 million jobs. The ICC projected that the loss in revenues would exceed $1.7 trillion in 2015, which is equivalent to 2% of the world economy. In addition to revenue losses, a variety of counterfeit products have been implicated in serious health and safety issues.

SUMMARY OF THE INVENTION

In one embodiment, the present invention provides a method of marking a cellulosic product for authentication: The method includes adding a detectable nucleic acid marker to a cellulosic medium during a step in a process for production of a cellulosic product; and thereby incorporating the nucleic acid marker into the cellulosic product to provide a detectably-marked cellulosic product. The preferred cellulosic product is lyocell.

In another embodiment, the present invention provides a method of authenticating a cellulosic product: The method includes: adding a detectable nucleic acid marker to a cellulosic medium during a step in a process for production of a cellulosic product; thereby incorporating the nucleic acid marker into the cellulosic product to provide a detectably-marked cellulosic product including the nucleic acid marker; introducing the detectably-marked cellulosic product into a stream of commerce; detecting the presence of the nucleic acid marker in the cellulosic medium of the detectably-marked cellulosic product; and thereby authenticating the cellulosic product.

The present invention further provides a detectably-marked cellulosic product for authentication, including a cellulosic medium that includes a detectable nucleic acid marker incorporated into the cellulosic medium and/or onto the surface of the cellulosic medium of the cellulosic product.

DETAILED DESCRIPTION

Figure 1:
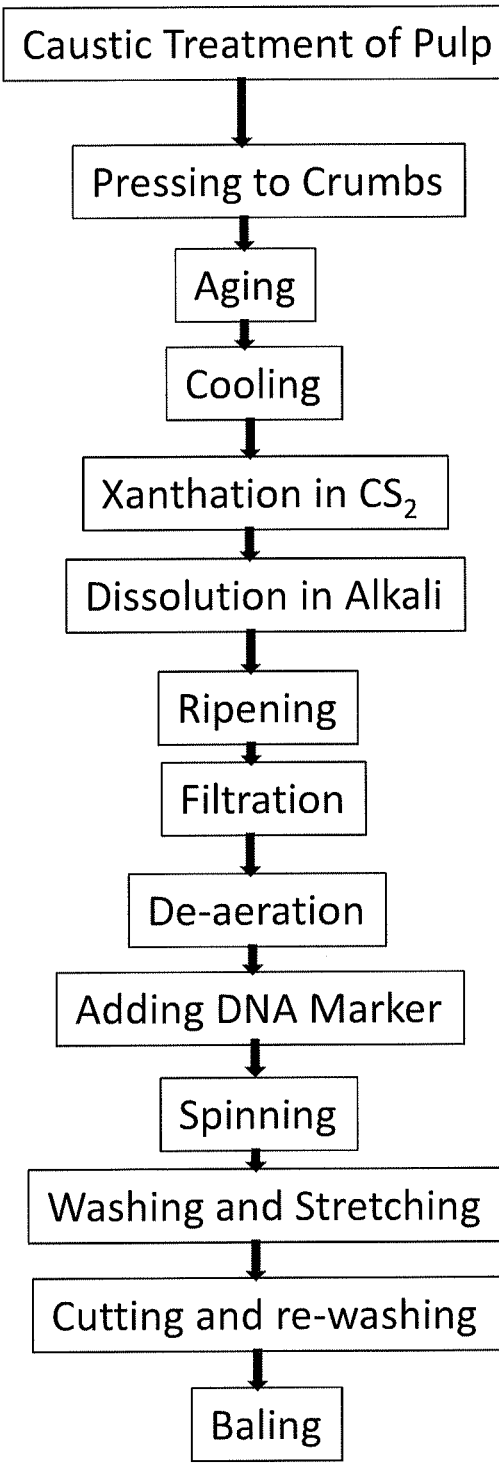
FIG. 1 shows a schematic of the steps of a process for the production of, a cellulosic fiber or film from cellulosic material.

Definitions of terms used herein:

"Cellulosic products" as used herein means cellulosic fibers such as for instance, viscose, lyocell or rayon; and cellulosic films, paper, cellulosic porous filters and cellulosic elastomeric sponges.

A "detectable nucleic acid marker" as used herein means any nucleic acid including at least in part, a unique sequence detectable by any of the many well known detection techniques, including polymerase chain reaction (PCR) techniques, other methods of DNA amplification such as isothermal, hybridization techniques and any of the well known method of DNA sequencing.

A "detectable marker DNA" as used herein means any DNA including at least in part, a unique sequence detectable by any of the many well known detection techniques, including polymerase chain reaction (PCR) techniques, other methods of DNA amplification such as isothermal, hybridization techniques and any of the well known method of DNA sequencing.

As used herein a "nucleic acid marker having a unique sequence" means a nucleic acid of one or more molecules having coherent nucleotide sequence shared by all the molecules.

As used herein "nucleic acid marker encoding information related to the product" means a nucleic acid marker having a nucleotide sequence designated to correlate with one or more segments of data related to the particular product. Such product-related information and the nucleotide sequence of the designated nucleic acid marker may be stored in a database. The database is useful for retrieving the product related information upon detection of the particular nucleotide sequence of the designated nucleic acid marker which thereby permits authentication or validation of the particular product from which the nucleic acid marker was obtained. The nucleic acid marker may be sampled at any stage during transit or in the stream of commerce to authenticate or validate the integrity of the product marked with the nucleic acid marker having the nucleotide sequence designated as related to the genuine product.

As used herein, "cellulosic material" includes plant matter (cotton, hemp, bamboo, and almost any botanical cellulosic material, as well as wood chips from beech, *eucalyptus*, and other trees). These cellulosic materials can be processed into a variety of different cellulosic products. Cellulosic materials are often mixed with solvents to manufacture cellulosic products.

A "cellulosic medium" may refer to any medium including cellulose, including but not limited to cellulosic dope. The cellulosic medium may include cellulose from one or more cellulosic materials. The cellulosic medium may be a slurry or liquid bath in which cellulose pulp and additional chemicals are combined.

Viscose rayon is a semi-synthetic cellulosic material composed of cellulose and cellulose xanthate. It is a soft fiber commonly used in fabrics and clothing, linings, shirts, shorts, coats, jackets, and other outerwear. Viscose is also used in industrial yarns such as cords incorporated in tire manufacturing, upholstery and carpets, and for casting cellophane films.

Rayon fibers are formed of regenerated cellulose and can be engineered to meet many different needs due to the wide range of properties attainable by variation of the production processes. Examples include high wet-modulus rayon yarn, super absorbent rayons and highly stretched low water retaining rayon fibers.

Cellulosic products also include lyocell, another form of rayon, and reconstituted cotton based products. Lyocell is a cellulosic rayon product manufactured from bleached wood pulp and is used for making textiles for clothing and other purposes. Cellophane is a clear wrapping formed as a cellulosic film instead of being spun into fibers.

In a preferred embodiment, the invention relates to a method of incorporating detectable marker DNA into lyocell cellulosic fibers by incorporating detectable marker DNA into the lyocell's cellulosic medium during the pre-spinning stages of the fiber's manufacturing process.

Schematic Process Steps

See FIG. 1 for a schematic of steps in the manufacturing of cellulosic products, including treatment of cellulosic pulp with a caustic soda solution; pressing of the alkaline treated cellulosic material to fluffy crumbs; aging of the cellulosic material at controlled temperature for a set time; a cooling step; a "xanthation" processing step using carbon disulfide ($CS_2$) treatment and dissolution in lye and dissolving the yellow crumbs in caustic soda; a filtration step; a ripening step in which the cellulosic material is matured; a de-aeration step; a pre-spinning step (at which the detectable marker nucleic acid may be added); a washing step; a stretching step followed by a cutting and re-washing of the cellulosic product; and a drying and baling into bales of cellulosic product for distribution or shipping to downstream manufacturers.

Figure 2:
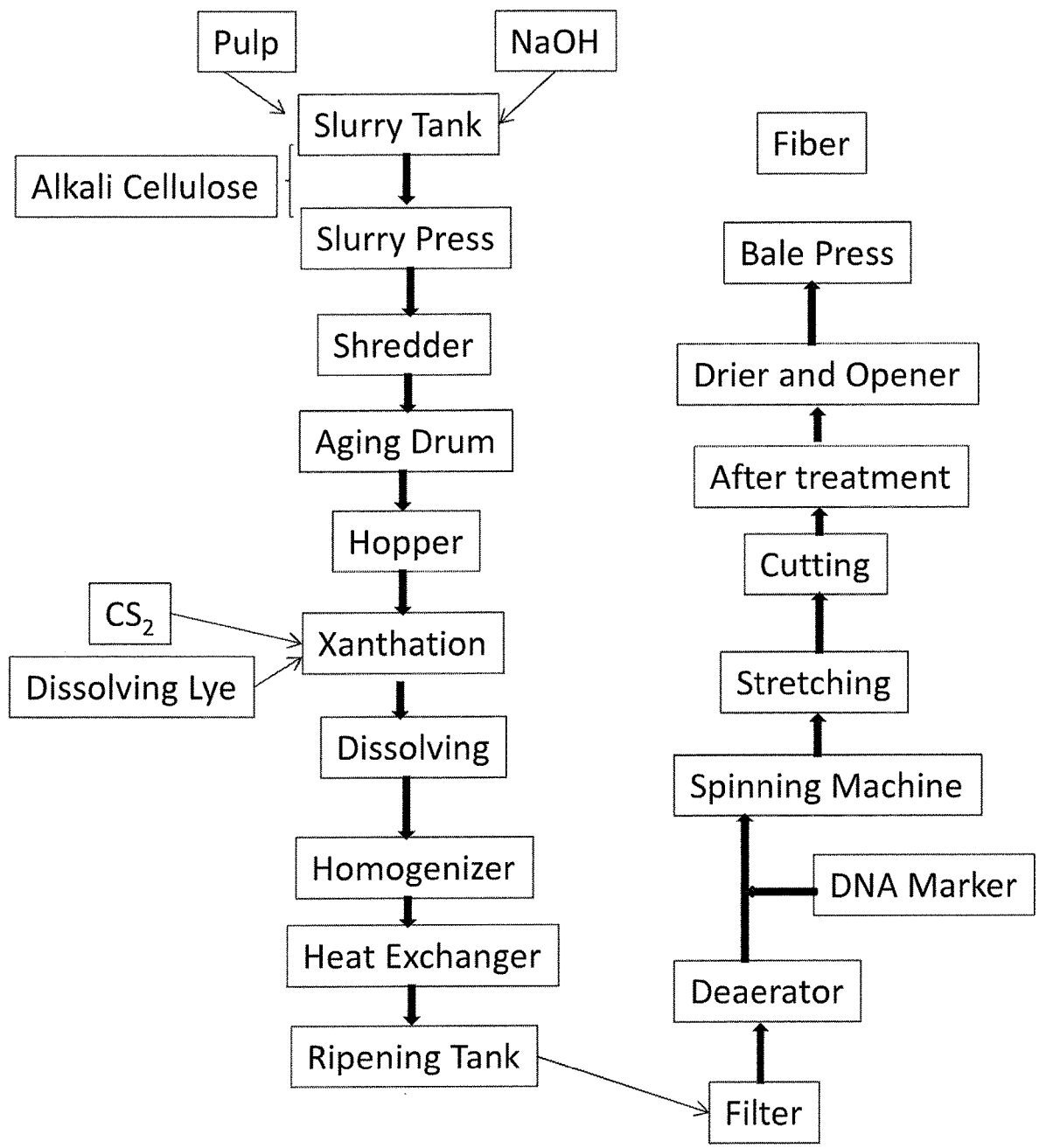
FIG. 2 shows a process for the production of a cellulosic fiber or film from wood chips, plant matter or other cellulosic material. One example of a step for addition of marker DNA is shown in the cellulosic medium immediately before spinning to produce the cellulosic fiber.

See FIG. 2 for a graphic representation of an exemplary process for the production of a cellulosic product showing addition of a DNA marker prior to spinning of fiber.

Figure 3:
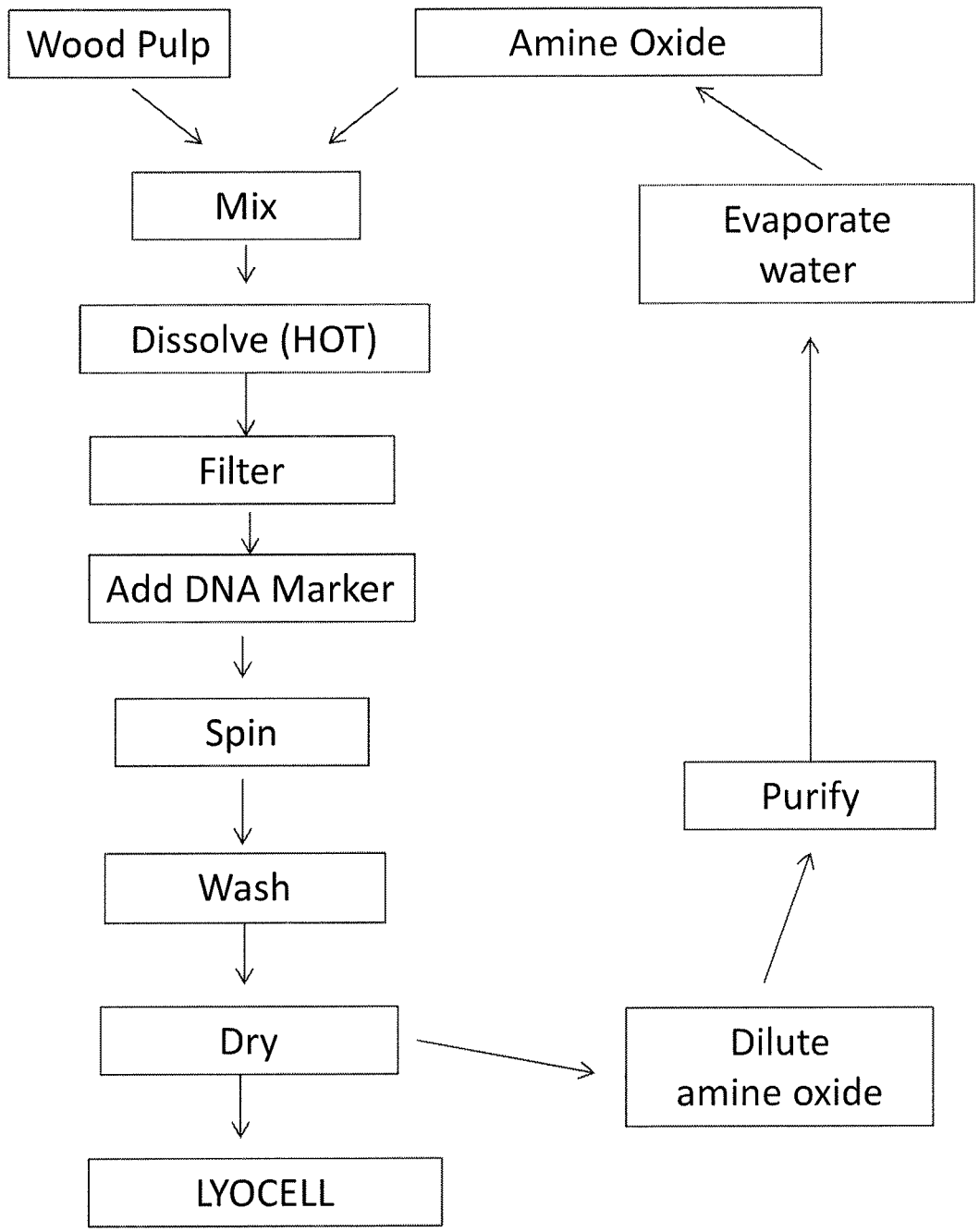
FIG. 3 shows the process of making lyocell, a cellulosic fiber.

See FIG. 3 for a schematic of steps in the manufacturing of lyocell. The process starts by mixing together wood pulp, water and amine oxide to create a cellulosic medium known as the cellulosic dope (The preferred amine oxide is N-methyl morpholine oxide (NMMO). The wood pulp dissolves into the solvent as a 1-1 mole complex of NMMO with water with heat and in a pressurized vessel. The solution is filtered. At this time, a detectable nucleic acid marker may be added to the cellulosic dope. Then, the cellulosic dope is pumped through spinnerets using the process of dry jet-wet spinning. After the spinning process, the fibers are washed with water and dried, then a lubricant may be applied to the fibers. The amine oxide solvent may be recovered from the fiber process and reused in the manufacturing process.

In an embodiment, the present invention provides a method of marking a cellulosic product for authentication: The method includes adding a detectable marker, such as for instance, and without limitation, a detectable nucleic acid to a cellulosic medium during a step in a process for production of a cellulosic product; and thereby incorporating and/or embedding the detectable marker into the cellulosic product to provide a detectably-marked cellulosic product. The step in the production of the cellulosic product may or may not be a step in which the cellulosic material is processed under alkaline conditions.

In one embodiment, the invention provides a method of marking a cellulosic product for authentication, including: adding a detectable nucleic acid marker to a cellulosic medium prior to or during the spinning or the filming of a cellulosic product, and thereby incorporating the detectable nucleic acid marker into the cellulosic product to provide a detectably-marked cellulosic product.

The detectably-marked cellulosic product produced by the above-listed methods may be any cellulosic fiber or cellulosic film.

Nucleic acids, especially deoxyribose nucleic acids (DNA) are well suited to use as detectable marker for ease of detection using modern methods such as isothermal amplification, polymerase chain reaction (PCR), and hybridization detection. Further, nucleic acids are ideally suited to encoding information due to the enormous coding capacity of DNA and RNA oligonucleotides. Useful information that can be readily encoded in nucleic acid detectable markers includes for instance and without limitation: the production lot number, the date of manufacture or processing, the time and the identity of the manufacturer.

Nucleic Acid Markers

Nucleic acids are particularly well suited to serve a detectable markers due to their enormous coding capacity and the fact that they can be used in such minute quantities that their sequences are impossible to duplicate without knowledge of their nucleotide sequences or access to a complementary probe or specific primer sequences necessary for their amplification and hence their detection.

The detectable nucleic acid marker is preferably attached directly onto or embedded directed into the cellulosic fibers or film. In the process of making lyocell, the nucleic acid marker should not be attached to any other "body" prior to being added to the cellulosic medium because adding a large "body" during the manufacturing process would degrade the internal structure of the end Lyocell fiber, which is typically less than 300 nm in width for lyocell. In fact, only trace (very small) amounts of detectable marker DNA are used in the process to ensure the uniform size and density of the internal fiber structure are not compromised.

Suitable amounts of detectable marker DNA for incorporation into the cellulosic material according to the present invention can range from 0.1 nanograms ($10^{-10}$ g) to micrograms ($10^{-6}$ g) of detectable marker DNA added per kilogram ($10^{-3}$ g) of cellulosic material, with a preferred range of 0.1 nanogram ($10^{-10}$ g) to 10 micrograms ($10 \times 10^{-6}$ g) of detectable marker DNA added per kilogram of cellulosic material. The quantity of detectable marker DNA added during the processing of the cellulosic material may be carefully metered for optimal delivery of suitable amounts of DNA for authentication, validation and tracking, yet ensuring the structural integrity of the delicate resultant cellulosic products.

For example, the amount of detectable marker DNA added in the method of making lyocell may range from micrograms ($10^{-6}$ g) to less than a nanogram ($10^{-9}$ g) per kilogram of cellulosic material. In a preferred embodiment, the amount of detectable marker DNA added to the cellulosic medium in the method of making lyocell may range from 0.1 nanograms ($10^{-10}$ g) to 10 micrograms ($10 \times 10^{-6}$ g) of detectable marker DNA added per kilogram of cellulosic material. In another embodiment, the amount of detectable marker DNA is less than 1 ppt ($10^{-17}$) w/w of the cellulosic material.

Suitable exemplary ranges of detectable marker DNA loading for cellulosic mediums include for instance:

A range from about 0.1 nanogram ($10^{-10}$ g) to about 10 microgram ($10 \times^{-6}$ g) of detectable marker DNA added per kilogram ($10^{-3}$ g) of cellulosic material.

A range from about 0.1 nanogram ($10 \times 10^{-10}$ g) to about 1 microgram ($10^{-3}$ g) of detectable marker DNA added per kilogram ($10^{-3}$ g) of cellulosic material.

A range from about 0.1 nanogram ($10 \times 10^{-10}$ g) to about 100 nanograms ($100 \times 10^{-9}$ g) of detectable marker DNA added per kilogram ($10^{-3}$ g) of cellulosic material.

A range from about 0.1 nanogram ($10 \times 10^{-10}$ g) to about 10 nanograms ($10 \times 10^{-9}$ g) of detectable marker DNA added per kilogram ($10^{-3}$ g) of cellulosic material.

A range from about 1 picograms ($1 \times 10^{-12}$ g) to about 100 microgram ($100 \times 10^{-6}$ g) of detectable marker DNA added per kilogram ($10^{-3}$ g) of cellulosic material.

A range from about 1 femtogram ($10^{-15}$ g) to about 1 microgram ($10^{-6}$ g) of detectable marker DNA added per kilogram ($10^{-3}$ g) of cellulosic material.

A range from about 10 femtograms ($10 \times 10^{-15}$ g) to about 100 nanograms ($100 \times 10^{-9}$ g) of detectable marker DNA added per kilogram ($10^{-3}$ g) of cellulosic material.

A range from about 100 femtograms ($100 \times 10^{-15}$ g) to about 10 nanograms ($10 \times 10^{-9}$ g) of detectable marker DNA added per kilogram ($10^{-3}$ g) of cellulosic material.

A range from about 1 picograms ($1 \times 10^{-12}$ g) to about 1 nanogram ($1 \times 10^{-9}$ g) of detectable marker DNA added per kilogram ($10^{-3}$ g) of cellulosic material.

Any minimum value set forth herein may be combined with any maximum value set forth herein to create all possible ranges.

The detectable marker DNA having a unique nucleotide sequence may be included with an excess of a carrier nucleic acid of a natural genomic sequence or a mixture of random synthetic or natural nucleic acid sequences. In this way, extraction of total nucleic acid will not reveal the detectable marker DNA sequence without access to the cognate PCR primer pair or pairs for PCR, or the complementary nucleotide hybridization probe depending on the detection method used.

The detectable marker DNA used in the methods of the present invention may be any suitable DNA marker. The DNA may be single or double stranded DNA. In one embodiment, the detectable marker DNA may be from about 20 bases to about 5,000 kilobases in single strand length, or about 20 base pairs to about 5 Kb pairs in double strand length.

Alkaline Activation

The detectable marker DNA as used herein may be alkaline activated before introduction of the markers to the cellulosic materials via a cellulosic medium.

In one embodiment, the detectable marker DNA used in the methods of the present invention may be alkaline activated as described in US patent application publication US 20140256881 A1 "Alkaline Activation For Immobilization of DNA Taggants" of Berrada et al. the entire disclosure of which is hereby incorporated by reference.

In one embodiment, the alkaline conditions are produced by mixing the detectable marker DNA with an alkaline solution having a high pH, for instance the pH of the alkaline solution can be a pH of about 9.0 or higher; a pH of about 10.0 or higher; a pH of about 11.0 or higher, or even a pH of about 12.0 or higher, and contacting the deoxyribonucleic acid that has been exposed to the alkaline conditions with the cellulosic medium. In one embodiment, the alkaline solution is a solution of a hydroxide of an alkali metal.

In one embodiment, the method including exposing the detectable marker DNA to alkaline conditions, includes contacting the deoxyribonucleic acid that has been exposed to the alkaline conditions with the cellulosic medium; wherein the alkaline conditions are produced by mixing the detectable marker DNA with a solution of an alkali metal hydroxide, the alkali metal hydroxide solution having a concentration of from about 1 mM to about 1.0 M.

Alternatively, the alkali metal hydroxide solution may have a concentration of from about 10 mM to about 0.9 M. In another embodiment, the alkali metal hydroxide solution may have a concentration of from about 0.1 M to about 0.8 M. In still another embodiment, the alkali metal hydroxide solution may have a concentration of from about 0.4 M to about 0.8 M. In another embodiment, the alkali metal hydroxide solution may have a concentration of about 0.6 M.

In one embodiment, the detectable marker DNA is mixed with an alkaline solution having a pH from about 9.0 to about 14.0 and incubated at a temperature of from about 5° C. to about 55° C. to produce the alkaline conditions. Alternatively, the detectable marker DNA may be mixed with an alkaline solution having a pH from about 9.0 to about 14.0 and incubated at a temperature of from about 0° C. to about 65° C. to produce the alkaline conditions and incubating the mixture for a period of from about 1 minute to about 6 hours. In another embodiment, the alkaline treated detectable marker DNA may be added to the cellulosic medium immediately, for instance and without limitation, the alkaline treated detectable marker DNA may be added to the cellulosic medium in a cellulosic bath immediately prior to spinning the cellulosic medium into fibers or created cellulosic film.

In one embodiment, NaOH may be used for alkaline activation for incorporation of aqueous nucleic acids. As a potential consequence of the presence of NaOH in the some of the cellulosic process(es), nucleic acids may become alkaline activated via a side reaction. Thus, NaOH may be used to prevent "coagulation" of the dissolved cellulose by normalizing pH. In addition, other caustic solutions may be employed, such as potassium hydroxide, calcium oxide, alkoxides, and/or butyl-lithium.

Non-Activated DNA

The addition of NMMO (N-Methylmorpholine N-oxide) to cellulosic material will dissolve the cellulosic material to form a cellulosic medium (cellulosic dope). Following the dissolution process(es) of the cellulosic materials, the detectable marker DNA is incorporated into the cellulosic medium immediately preceding or during the re-polymerization/spinning step(s) for marking and authentication purposes. In this embodiment, the detectable marker DNA will not be alkaline activated.

In an exemplary embodiment, the detectable marker DNA is not alkaline activated, and is added to a cellulosic medium comprising wood pulp, NMMO and water, after dissolution of the cellulosic materials, but immediately preceding or during the re-polymerization/spinning step(s). In this instance, the detectable marker DNA may be delivered into the cellulosic medium as a saturated bound complex with a protecting agent, the protecting agent chosen from the following compounds: non aromatic alkyl amines such as tri-butyl amine, aromatic (triphenyl) alkyl amines such as crystal violet or methyl green, biological amines such as sperinidine or spermine. The protecting agent acts to protect the detectable marker DNA from degradation caused by various aspects of the cellulosic medium, including but not limited to NMMO.

Metal ions, especially divalent metal ions are known to catalyze the hydrolytic degradation of nucleic acids. Therefore, addition of these metal ions in water and additives should be avoided where possible. Low concentrations of divalent metal ions commonly found in ground water can be removed by the addition of chelating agents.

The use of low concentrations of about 1 mM to about 20 mM of chelating agents such as Tris-EDTA for the sequestration of metal ions is well documented: See for instance "Metal Ion/Buffer Interactions" Fischer et al. (1979) Eur. J. Biochem. vol. 94: 523-530.

Alternatively, water softeners (e.g., amino acids such as glutamic acid and histidine, or organic dicarboxylic acids such as malate, and polypeptides such as phytochelatin, etc) may be used to sequester and or chelate metal ions, especially divalent metal ions.

Water quality can be a problem leading to lack of stability of the DNA detectable marker: this was found in many cases to be remedied by improving the water quality by removing divalent metal ions with a chelating agent.

Incorporation of Detectable Marker DNA

Surface coating of detectable marker DNA onto a cellulosic product exposes the detectable marker DNA to any further treatments and downstream processing which may lead to reduction in the amount of the detectable marker DNA surviving the processing, but this may be addressed by heavier initial loading of the detectable marker DNA onto the surface of the cellulosic product.

Incorporation of a detectable DNA marker by encapsulation within the cellulosic product rather than coating onto the surface of the cellulosic product protects the detectable DNA marker and preserve the ability to amplify the DNA by standard methods such as PCR and isothermal amplification for authentication. In another embodiment, the detectable DNA marker is integrated uniformly into the cellulosic fiber core and thus is protected from further downstream processing. Such encapsulation may require harsher conditions for extraction of the detectable DNA marker for adequate and reliable detection.

The detectable DNA marker may be added to the cellulosic material, via addition to the cellulosic medium, at any stage of the manufacturing of the cellulosic product. In one exemplary process, the detectable DNA marker may be added to the cellulosic material via addition to the cellulosic medium at the stage immediately before spinning/repolymerization into cellulosic fibers or extruding through a slit to form a cellulosic film. This procedure provides a cellulosic product which incorporates the detectable DNA marker throughout the cellulosic fiber or cellulosic film. The detectable DNA marker is present in the interior of the fiber or film as well as on the surface and so it is at least partially shielded from any further harsh treatments to which the cellulosic product may be exposed.

Alternatively, the detectable DNA marker may be applied to the surface of the cellulosic fibers or the cellulosic film. Higher loadings of the detectable DNA marker may be used to provide greater recoverability of the detectable DNA marker after surface treatments that may cause loss of some of the detectable DNA marker.

In another embodiment, the present invention provides a method of authenticating a cellulosic product including: adding a detectable marker such as for instance, and without limitation, a detectable nucleic acid encoding information related to the production process and/or the cellulosic product, to a cellulosic medium during a step in a process for production of a cellulosic product; thereby incorporating the detectable marker into the cellulosic product to provide a detectably-marked cellulosic product; introducing the detectably-marked cellulosic product into a stream of commerce; detecting the presence of the detectable marker in the cellulosic medium of the detectably-marked cellulosic product; and thereby authenticating the cellulosic product.

In another embodiment, the invention provides a method of authenticating a cellulosic product, including: adding a detectable nucleic acid marker to a cellulosic medium prior to or during the spinning or the filming of a cellulosic product; thereby incorporating the detectable nucleic acid marker into the cellulosic product to provide a detectably-marked cellulosic product; introducing the detectably-marked cellulosic product into a stream of commerce; detecting the presence of the detectable nucleic acid marker in the cellulosic medium of the detectably-marked cellulosic product; and thereby authenticating the cellulosic product. The cellulosic product may be any cellulosic product, such as for instance paper, or a cellulosic fiber, e.g. rayon, or a cellulosic film such as cellophane, a porous cellulosic filter, or an elastomeric cellulosic sponge.

The detectable nucleic acid marker may be a detectable DNA marker having a unique nucleotide sequence. In one embodiment, the unique nucleotide sequence of the detectable DNA marker may be used to encode information related to the process for production of the cellulosic product. The detectable DNA marker may or may not be alkaline activated prior to addition to the cellulosic medium during the cellulosic production process and may impart specific information about the cellulosic product, such as for instance, and without limitation, a production lot number, a date, a time and a manufacturer identity.

The present invention further provides a detectably marked a cellulosic product for authentication, including a cellulosic medium and a detectable marker, such as a nucleic acid marker incorporated into the cellulosic medium and/or onto the surface of the cellulosic product to form a detectably marked a cellulosic product.

In the event of a conflict between a definition recited in this specification and a definition provided in a patent or publication incorporated herein by reference, the definition provided herein is intended.

The disclosures of each of the references, patents and published patent applications disclosed herein are each hereby incorporated by reference herein in their entireties.

While the invention has been shown and described with reference to exemplary embodiments thereof, it will be understood by those of ordinary skill in the art that various changes in form and detail may be made therein without departing from the spirit and scope of the invention.

EXAMPLES

Example 1. DNA Tagging of Lyocell Dope (Cellulosic Material)

Wood pulp is mixed with defined mass excess solution of 50% NMMO, 50% water at room temperature to form a cellulosic medium. The cellulosic medium is then heated to solvate the cellulose and evaporate excess water to form the cellulosic medium.

DNA concentrate comprising detectable marker DNA is added to the cellulosic medium, at one of two (2) different times during the manufacturing process: The final mass ratio of detectable DNA marker to cellulosic material is typically between 0.1 nanograms to 10 micrograms per kilogram of cellulosic material. The addition point are:

A. Addition of detectable DNA marker at the beginning the heating period.

B. Addition of detectable DNA marker after the heating period, just before extrusion/spinning to form fiber.

Example 2. DNA Recovery from Lyocell Fibers

Four methods of DNA recovery and analysis from the lyocell may be used.
Method 1
Two-step in situ PCR of fiber, followed by standard CE (capillary electrophoresis):
 based on use of @10 mg (i.e 10 µL) of fiber per test. Fiber is added directly to a 40 uL PCR reaction
Aqueous extraction of Fiber at 90° C. at pH 8 or greater, followed by charge switch magnetic bead concentration, then PCR/CE:
 based on the use of @100 mg (i.e 100 µL) of fiber per test.
Method 2
Aqueous extraction of fiber at 90° C. at pH 8 or greater, followed by charge switch magnetic bead concentration, followed by qPCR:
 based on use of @100 mg (i.e 100 µL) of fiber per test. An optimized DNA TaqMan assay may be deployed on a qPCR device
Method 3
Solvation of fiber in 24% NaOH at 90° C. for 10 minutes, followed by neutralization with acetate and Nynal Magnetic Bead concentration, followed by qPCR:
 based on the use of @100 mg (i.e 100 µL) of fiber per test. An optimized DNA TaqMan assay may be deployed on a qPCR device
Method 4
Solvation of fiber in 50% NMMO, 50% water at 90° C. followed by neutralization with acetate and Nynal Magnetic Bead concentration, followed by qPCR:
 based on the use of @100 mg (i.e 100 µL) of fiber per test. An optimized DNA TaqMan assay may be deployed on a qPCR device

The invention claimed is:

1. A method of authenticating a cellulosic product, comprising:
 adding a detectable nucleic acid marker to a cellulosic medium during the manufacturing process for a cellulosic product, said cellulosic medium containing at least a cellulosic material and a solvent; and
 thereby incorporating the detectable nucleic acid marker into the cellulosic product to provide a nucleic acid-marked cellulosic product;
 introducing the nucleic acid-marked cellulosic product into a stream of commerce;
 detecting the presence of the detectable nucleic acid marker in the cellulosic product via dissolving all or a portion of the nucleic acid-marked cellulosic product into a solution and performing a PCR based detection technique on a sample of said solution; and
 thereby authenticating the cellulosic product.

2. The method according to claim 1, wherein the detectable nucleic acid marker comprises a detectable DNA marker.

3. The method according to claim 2, wherein the detectable DNA marker is added to the cellulosic medium in an amount ranging from 1 nanogram to 1 microgram of DNA per kilogram of cellulosic material.

4. The method according to claim 2, wherein the detectable DNA marker is added to the cellulosic medium in an amount ranging from 0.1 nanograms to 10 micrograms of DNA per kilogram of cellulosic material.

5. The method according to claim 2, wherein at least one of N-methylmorpholine-N-oxide (NMMO) or sodium hydroxide is used to dissolve all or a portion of the nucleic acid-marked cellulosic product into a solution.

6. The method according to claim 5, wherein information related to the process for production of the cellulosic product comprises one or more of a production lot number, a date, a time and a manufacturer.

7. The method according to claim 1, wherein the cellulosic product is a cellulosic fiber.

8. The method according to claim 7, wherein the cellulosic fiber is lyocell.

9. The method according to claim 7, wherein the cellulosic fiber is reconstituted cotton.

10. The method according to claim 1, wherein the cellulosic material is cotton.

11. A method of authenticating a cellulosic product, comprising:
 adding a detectable nucleic acid marker to the surface of a cellulosic fiber during the production process of said cellulosic fiber; and
 thereby incorporating the detectable nucleic acid marker onto the cellulosic fiber to provide a nucleic acid-marked cellulosic fiber;
 manufacturing a cellulosic product comprised partially or entirely of said nucleic acid-marked cellulosic fiber to provide a nucleic acid-marked cellulosic product;
 introducing the nucleic acid-marked cellulosic produce into a stream of commerce;
 detecting the presence of the nucleic acid marked cellulosic fiber in the cellulosic product via dissolving all or a portion of the cellulosic product into a solution and performing a PCR based detection technique on a sample of said solution; and
 thereby authenticating the cellulosic product.

12. The method according to claim 11, wherein the detectable nucleic acid marker comprises a detectable DNA marker.

13. The method according to claim 11, wherein the detectable DNA marker is added to the cellulosic fiber in an amount ranging from 1 nanogram to 1 microgram of DNA per kilogram of cellulosic fiber.

14. The method according to claim 11, wherein the detectable DNA marker is added to the cellulosic fiber in an amount ranging from 0.1 nanograms to 10 micrograms of DNA per kilogram of cellulosic fiber.

15. The method according to claim 11, wherein at least one of N-methylmorpholine-N-oxide (NMMO) or sodium hydroxide is used to dissolve all or a portion of the nucleic acid-marked cellulosic product into a solution.

16. The method according to claim 11, wherein information related to the process for production of the cellulosic product comprises one or more of a production lot number, a date, a time and a manufacturer.

17. The method according to claim 11, wherein the cellulosic fiber is lyocell.

18. The method according to claim 11, wherein the cellulosic fiber is rayon.

19. The method according to claim 11, wherein the cellulosic fiber is reconstituted cotton.

* * * * *